United States Patent
Kimura et al.

(10) Patent No.: US 9,603,756 B2
(45) Date of Patent: Mar. 28, 2017

(54) COMPOSITE MATERIAL FOR ABSORBENT ARTICLE, AND METHOD FOR MANUFACTURING THEREOF

(71) Applicant: UNICHARM CORPORATION, Shikokuchuo-shi, Ehime (JP)

(72) Inventors: Akihiro Kimura, Kanonji (JP); Hiroyuki Muto, Toyohashi (JP); Norio Hakiri, Toyohashi (JP); Hideyo Yoshikawa, Toyohashi (JP); Atsunori Matsuda, Toyohashi (JP); Go Kawamura, Toyohashi (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 15/034,923

(22) PCT Filed: Nov. 4, 2014

(86) PCT No.: PCT/JP2014/079211
§ 371 (c)(1),
(2) Date: May 6, 2016

(87) PCT Pub. No.: WO2015/068684
PCT Pub. Date: May 14, 2015

(65) Prior Publication Data
US 2016/0287451 A1      Oct. 6, 2016

(30) Foreign Application Priority Data

Nov. 7, 2013  (JP) ................................. 2013-231460
Nov. 7, 2013  (JP) ................................. 2013-231475

(51) Int. Cl.
*B01J 20/26* (2006.01)
*A61F 13/53* (2006.01)
*D06M 15/263* (2006.01)
*A61F 13/00* (2006.01)
*D06M 15/356* (2006.01)
*B32B 5/02* (2006.01)
*B32B 7/02* (2006.01)
*B32B 27/12* (2006.01)
*B01J 20/28* (2006.01)
*B01J 20/32* (2006.01)
*C08J 3/12* (2006.01)
*D06M 15/21* (2006.01)
*D06M 101/32* (2006.01)

(52) U.S. Cl.
CPC ........ *A61F 13/53* (2013.01); *A61F 13/00008* (2013.01); *B01J 20/261* (2013.01); *B01J 20/262* (2013.01); *B01J 20/28023* (2013.01); *B01J 20/3231* (2013.01); *B01J 20/3293* (2013.01); *B32B 5/022* (2013.01); *B32B 7/02* (2013.01); *B32B 27/12* (2013.01); *C08J 3/126* (2013.01); *D06M 15/21* (2013.01); *D06M 15/263* (2013.01); *D06M 15/3562* (2013.01); *A61F 2013/530131* (2013.01); *A61F 2013/530481* (2013.01); *B32B 2262/02* (2013.01); *B32B 2307/726* (2013.01); *B32B 2555/02* (2013.01); *C08J 2300/14* (2013.01); *C08J 2433/02* (2013.01); *C08J 2439/00* (2013.01); *D06M 2101/32* (2013.01)

(58) Field of Classification Search
CPC ................................. B01J 20/26; B01J 20/32
USPC ......................................................... 502/402
See application file for complete search history.

(56) References Cited

U.S. PATENT DOCUMENTS

| | | |
|---|---|---|
| 5,382,610 A | 1/1995 | Harada et al. |
| 2002/0088579 A1 | 7/2002 | Forsberg et al. |
| 2003/0064222 A1 | 4/2003 | Nakamura et al. |
| 2006/0153988 A1 | 7/2006 | Nomura et al. |
| 2009/0264845 A1 | 10/2009 | Himori et al. |
| 2009/0275906 A1 | 11/2009 | Berland et al. |
| 2011/0197369 A1 | 8/2011 | Hinestroza et al. |

FOREIGN PATENT DOCUMENTS

| | | |
|---|---|---|
| DE | 102006062113 A1 | 6/2008 |
| EP | 2106466 B1 | 9/2013 |

(Continued)

OTHER PUBLICATIONS

Hiroyuki Muto, "Creation of Nanointegrated Structure by Electrostatic Adsorption Compositing Method and Production of Fine Structure-Controlled Functional Composite", Expected Materials for the Future, Nov. 10, 2011, pp. 52-57, vol. 11, No. 11, NTS Inc, Japan.

(Continued)

*Primary Examiner* — Edward Johnson
(74) *Attorney, Agent, or Firm* — Hauptman Ham, LLP

(57) ABSTRACT

A composite material for an absorbent article and a method for manufacturing said composite material, said composite material being obtained by causing an absorbent material to adhere by electrostatic interaction to a substrate material, the surface of the absorbent material being positively or negatively charged in a prescribed solvent selected from among a nonpolar organic solvent, a polar organic solvent, and a water/polar organic solvent mixture; and the surface of the composite material being charged to an electrical charge opposite to that of the surface of the substrate material, in the prescribed solvent. The substrate material has a fiber substrate or a plastic substrate, and a polyelectrolyte layer provided on the surface layer; and/or the absorbent material has an absorbent-particle substrate or an absorbent fiber substrate, and a polyelectrolyte layer provided on the surface layer.

20 Claims, 1 Drawing Sheet

(56) References Cited

FOREIGN PATENT DOCUMENTS

| | | |
|---|---|---|
| JP | 46-17282 B | 5/1971 |
| JP | 5-96159 A | 4/1993 |
| JP | 6-341044 A | 12/1994 |
| JP | 11-77908 A | 3/1999 |
| JP | 2005-516075 A | 6/2005 |
| JP | 2009-174114 A | 8/2009 |
| JP | 2010-64945 A | 3/2010 |
| JP | 2013-39804 A | 2/2013 |
| WO | 03/002089 A1 | 1/2003 |
| WO | 2004/022840 A1 | 3/2004 |
| WO | 2006/011625 A1 | 2/2006 |
| WO | 2008/077372 A2 | 7/2008 |
| WO | 2010/004630 A1 | 1/2010 |

OTHER PUBLICATIONS

International Search Report in International Application No. PCT/JP2014/079211, mailed Jan. 27, 2015.

COMPOSITE MATERIAL FOR ABSORBENT ARTICLE, AND METHOD FOR MANUFACTURING THEREOF

RELATED APPLICATIONS

The present application is a National Phase of International Application Number PCT/JP2014/079211 filed Nov. 4, 2014 and claims priority to Japanese Application Number 2013-231460 filed Nov. 7, 2013 and Japanese Application Number 2013-231475filed Nov. 7, 2013.

TECHNICAL FIELD

The present invention relates to a composite material for absorbent articles and a method for producing the same.

BACKGROUND ART

As a method for loading particles on a surface of a thermoplastic resin fiber,
a method in which particles are fixed to the surface of the thermoplastic resin fiber with an adhesive (a binder) (Patent Literature 1), a method in which particles heated to a temperature which is higher that the melting point of a thermoplastic resin fiber are contacted to the thermoplastic resin fiber to fuse the particles to the surface of the thermoplastic resin fiber (Patent Literature 2), etc., are known.

Meanwhile, as a method for adsorbing child particles onto mother particles, a method in which the surfaces of the mother particles and child particles are coated respectively with polyelectrolytes that are electrostatically charged to electric charges opposite to each other (cationic polymer or anionic polymer), thereby allowing the child particles to be adsorbed on the mother particles by electrostatic interaction (Patent Literature 3).

CITATION LIST

Patent Literature

Patent Literature 1: Japanese Unexamined Patent Publication No. H6-341044
Patent Literature 2: Japanese Unexamined Patent Publication No. 2009-174114
Patent Literature 3: Japanese Unexamined Patent Publication No. 2010-64945

SUMMARY OF INVENTION

Problems to be Solved by the Invention

However, in the method described in Patent Literature 1, the surface of the particles are excessively covered with the adhesive (binder), and accordingly, there is a possibility that the particles cannot demonstrate the desired functions effectively.

Further, when the particles contain a material the properties of which vary with heating, the method descried in Patent Literature 2 is not appropriate. For example, when the particles are superabsorbent resin particles, if the superabsorbent resin particles are crosslinked with heating, the expansion of the superabsorbent resin particles due to water absorption is prevented by the crosslinking, and therefore there is a possibility that the water absorbing performance of the superabsorbent resin particles is decreased.

Further, in the method described in Patent Literature 2, the particles are embedded in the fibers, and therefore, if the particles are intended to demonstrate their functions by expansion, the method described in Patent Literature 2 is not appropriate. For example, when the particles are superabsorbent resin particles, if the superabsorbent resin particles are embedded in a fiber, the expansion of the superabsorbent resin particles due to water absorption is prevented by the embedment, and therefore there is a possibility that the water absorbing performance of the superabsorbent resin particles is decreased.

Accordingly, the present invention is directed to provide a composite material for absorbent articles, comprising a substrate material and a water absorbent material composited together without an adhesive, without heating, and without the water absorbent material being embedded in the substrate material. The present invention is further directed to provide a method for producing a composite material for absorbent articles, whereby a substrate material and a water absorbent material can be composited together without an adhesive, without heating, and without embedding the water absorbent material in the substrate material.

Solution to Problem

In order to solve the above problems, the present invention provides a composite material for an absorbent article, comprising a substrate material having a surface which is positively or negatively electrostatically charged in a predetermined solvent selected from a non-polar organic solvent, a polar organic solvent, and a mixed solvent of a polar organic solvent and water, and a water absorbent material adsorbed thereon by electrostatic interaction, having a surface which is electrostatically charged to an electric charge opposite to that of the surface of the substrate material, wherein the substrate material comprises a fibrous base material or resinous base material and a polyelectrolyte layer provided in a surface layer thereof, and/or, the water absorbent material has a water absorbent particulate base material or water absorbent fibrous base material and a polyelectrolyte layer provided in a surface layer thereof. The present invention further provides a method for producing a composite material for an absorbent article, comprising an adsorption step in which, in a predetermined solvent selected from a non-polar organic solvent, a polar organic solvent, and a mixed solvent of a polar organic solvent and water, a substrate material having a surface which is positively or negatively electrostatically charged in the predetermined solvent is contacted with a water absorbent material having a surface which is electrostatically charged to an electric charge opposite to that of the surface of the substrate material to adsorb the water absorbent material onto the substrate material by electrostatic interaction, wherein the substrate material comprises a fibrous base material or resinous base material and a polyelectrolyte layer provided in a surface layer thereof, and/or, the water absorbent material has a water absorbent particulate base material or water absorbent fibrous base material and a polyelectrolyte layer provided in a surface layer thereof.

In a preferred embodiment (Embodiment 1) of the composite material of the present invention, the substrate material and/or the water absorbent material have a plurality of polyelectrolyte layers stacked together, and in the plurality of polyelectrolyte layers, polyelectrolyte layers that are electrostatically charged to electric charges opposite to each other in the predetermined solvent are adjacent to each other.

In another preferred embodiment (Embodiment 2) of the composite material of the present invention, the substrate material and water absorbent material have a zeta potential of 20 mV or more in absolute value in the predetermined solvent, and are balanced in electric charge. Embodiment 2 can be combined with Embodiment 1.

In another preferred embodiment (Embodiment 3) of the composite material of the present invention, the substrate material is a second or (m+1)-th coated material produced by a method comprising the following steps ($a_1$) to ($c_1$):

($a_1$) contacting, in a predetermined solvent selected from water, a non-polar organic solvent, a polar organic solvent, and a mixed solvent of a polar organic solvent and water, a fibrous base material or resinous base material having a surface which is positively or negatively electrostatically charged in the predetermined solvent with a polyelectrolyte which is electrostatically charged to an electric charge opposite to that of the surface of the fibrous base material or resinous base material in the predetermined solvent to produce a first coated material having in a surface layer thereof a first polyelectrolyte layer;

($b_1$) contacting, in a predetermined solvent selected from water, a non-polar organic solvent, a polar organic solvent, and a mixed solvent of a polar organic solvent and water, a $k_1$-th coated material, wherein $k_1$ is an integer of 1 or more, having in a surface layer thereof a $k_1$-th polyelectrolyte layer which is positively or negatively electrostatically charged in the predetermined solvent with a polyelectrolyte which is electrostatically charged to an electric charge opposite to that of the $k_1$-th polyelectrolyte layer in the predetermined solvent to produce a ($k_1$+1)-th coated material having in a surface layer thereof a ($k_1$+1)-th polyelectrolyte layer; and ($c_1$) performing step ($b_1$) at $k_1=1$ to produce a second coated material having in a surface layer thereof a second polyelectrolyte layer, or performing step ($b_1$) repeatedly from $k_1=1$ to $k_1=m$, wherein m is an integer of 2 or more, to produce a (m+1)-th coated material having in a surface thereof a (m+1)-th polyelectrolyte layer. Embodiment 3 can be combined with Embodiment 1 and/or Embodiment 2.

In one preferred embodiment (Embodiment 4) of Embodiment 3, the second or (m+1)-th coated material has a zeta potential of 20 mV or more in absolute value.

In another preferred embodiment (Embodiment 5) of the composite material of the present invention, the water absorbent material is a second or (n+1)-th coated material produced by a method comprising the following step ($a_2$) to ($c_2$):

($a_2$) contacting, in a predetermined solvent selected from a non-polar organic solvent, a polar organic solvent, and a mixed solvent of a polar organic solvent and water, a water absorbent particulate base material or water absorbent fibrous base material having a surface which is positively or negatively electrostatically charged in the predetermined solvent with a polyelectrolyte which is electrostatically charged to an electric charge opposite to that of the surface of the water absorbent particulate base material or water absorbent fibrous base material in the predetermined solvent to produce a first coated material having in a surface layer thereof a first polyelectrolyte layer;

($b_2$) contacting, in a predetermined solvent selected from a non-polar organic solvent, a polar organic solvent, and a mixed solvent of a polar organic solvent and water, a $k_2$-th coated material, wherein $k_2$ is an integer of 1 or more, having in a surface layer thereof a $k_2$-th polyelectrolyte layer which is positively or negatively electrostatically charged in the predetermined solvent with a polyelectrolyte which is electrostatically charged to an electric charge opposite to that of the $k_2$-th polyelectrolyte layer in the predetermined solvent to produce a ($k_2$+1)-th coated material having in a surface layer thereof a ($k_2$+1)-th polyelectrolyte layer; and ($c_2$) performing step ($b_2$) at $k_2=1$ to produce a second coated material having in a surface layer thereof a second polyelectrolyte layer, or performing step ($b_2$) repeatedly from $k_2=1$ to $k_2=n$, wherein n is an integer of 2 or more, to produce a (n+1)-th coated material having in a surface layer thereof a (n+1)-th polyelectrolyte layer. Embodiment 5 can be combined with one or more of Embodiments 1 to 4.

In one preferred embodiment (Embodiment 6) of Embodiment 5, the second or (n+1)-th coated material has a zeta potential of 20 mV or more in absolute value.

In another preferred embodiment (Embodiment 7) of the composite material of the present invention, the polar organic solvent is a monohydric alcohol having 1 to 3 carbon atoms. Embodiment 7 can be combined with one or more of Embodiments 1 to 6.

In another preferred embodiment (Embodiment 8) of the composite material of the present invention, the fibrous base material of the substrate material is a thermoplastic resin fiber or aggregates thereof. Embodiment 8 can be combined with one or more of Embodiments 1 to 7.

In another preferred embodiment (Embodiment 9) of the composite material of the present invention, the fibrous base material or resinous base material of the substrate material is a nonwoven fabric sheet or resin sheet. Embodiment 9 can be combined with one or more of Embodiments 1 to 8.

In one preferred embodiment (Embodiment 1) of the production method of the present invention, the substrate material and/or the water absorbent material have a plurality of polyelectrolyte layers stacked together, and in the plurality of polyelectrolyte layers, polyelectrolyte layers that are electrostatically charged to electric charges opposite to each other in the predetermined solvent are adjacent to each other.

In another preferred embodiment (Embodiment 2) of the production method of the present invention, the substrate material and water absorbent material have a zeta potential of 20 mV or more in absolute value in the predetermined solvent, and are balanced in charge. Embodiment 2 can be combined with Embodiment 1.

Another preferred embodiment (Embodiment 3) of the production method of the present invention comprises the following steps ($a_1$) to ($c_1$):

($a_1$) contacting, in a predetermined solvent selected from water, a non-polar organic solvent, a polar organic solvent, and a mixed solvent of a polar organic solvent and water, a fibrous base material or resinous base material having a surface which is positively or negatively electrostatically charged in the predetermined solvent with a polyelectrolyte which is electrostatically charged to an electric charge opposite to that of the surface of the fibrous base material or resinous base material in the predetermined solvent to produce a first coated material having in a surface layer thereof a first polyelectrolyte layer;

($b_1$) contacting, in a predetermined solvent selected from water, a non-polar organic solvent, a polar organic solvent, and a mixed solvent of a polar organic solvent and water, a $k_1$-th coated material, wherein $k_1$ is an integer of 1 or more, having in a surface layer thereof a $k_1$-th polyelectrolyte layer which is positively or negatively electrostatically charged in the predetermined solvent with a polyelectrolyte which is electrostatically charged to an electric charge opposite to that of the $k_1$-th polyelectrolyte layer in the predetermined solvent to produce a ($k_1$+1)-th coated material having in a surface layer thereof a ($k_1$+1)-th polyelectrolyte layer; and ($c_1$) performing step ($b_1$) at $k_1=1$ to produce a second coated material having in a surface layer thereof a second polyelectrolyte layer, or performing step ($b_1$) repeatedly from $k_1=1$ to $k_1=m$, wherein m is an integer of 2 or more, to produce a (m+1)-th coated material having in a surface layer thereof a (m+1)-th polyelectrolyte layer;

wherein the second or (m+1)-th coated material is used as the substrate material. Embodiment 3 can be combined with one or more of Embodiment 1 and/or Embodiment 2.

In one preferred embodiment (Embodiment 4) of Embodiment 3, the second or (m+1)-th coated material has a of zeta potential of 20 mV or more in absolute value.

Another preferred embodiment (Embodiment 5) of the production method of the present invention comprises the following steps ($a_2$) to ($c_2$):

($a_2$) contacting, in a predetermined solvent selected from a non-polar organic solvent, a polar organic solvent, and a mixed solvent of a polar organic solvent and water, a water absorbent particulate base material or water absorbent fibrous base material having a surface which is positively or negatively electrostatically charged in the predetermined solvent with a polyelectrolyte which is electrostatically charged to an electric charge opposite to that of the surface of the water absorbent particulate base material or water absorbent fibrous base material in the predetermined solvent to produce a first coated material having in a surface layer thereof a first polyelectrolyte layer;

($b_2$) contacting, in a predetermined solvent selected from a non-polar organic solvent, a polar organic solvent, and a mixed solvent of a polar organic solvent and water, a $k_2$-th coated material, wherein $k_2$ is an integer of 1 or more, having in a surface layer thereof a $k_2$-th polyelectrolyte layer which is positively or negatively electrostatically charged in the predetermined solvent with the polyelectrolyte which is electrostatically charged to an electric charge opposite to that of the $k_2$-th polyelectrolyte layer in the predetermined solvent to produce a ($k_2$+1)-th coated material having in a surface layer thereof a ($k_2$+1)-th polyelectrolyte layer; and ($c_2$) performing step ($b_2$) at $k_2=1$ to produce a second coated material having in a surface layer thereof a second polyelectrolyte layer, or performing step ($b_2$) repeatedly from $k_2=1$ to $k_2=n$, wherein n is an integer of 2 or more, to produce a (n+1)-th coated material having in a surface layer thereof a (n+1)-th polyelectrolyte layer;

wherein the second or (n+1)-th coated material is used as the water absorbent material. Embodiment 5 can be combined with one or more of Embodiments 1 to 4.

In one preferred embodiment (Embodiment 6) of Embodiment 5, wherein the second or (n+1)-th coated material has a zeta potential of 20 mV or more in absolute value.

In another preferred embodiment (Embodiment 7) of the production method of the present invention, the polar organic solvent is a monohydric alcohol having 1 to 3 carbon atoms. Embodiment 7 can be combined with one or more of Embodiments 1 to 6.

In another preferred embodiment (Embodiment 8) of the production method of the present invention, the fibrous base material of the substrate material is a thermoplastic resin fiber or aggregates thereof. Embodiment 8 can be combined with one or more of Embodiments 1 to 7.

In another preferred embodiment (Embodiment 9) of the production method of the present invention, the fibrous base material or resinous base material of the substrate material is a nonwoven fabric sheet or resin sheet. Embodiment 9 can be combined with one or more of Embodiments 1 to 8.

Effects of the Invention

According to the present invention, a composite material for absorbent articles, comprising a substrate material and a water absorbent material composited together without an adhesive, without being heating, and without the water absorbent material being embedded in the substrate material, is provided. According to the present invention, a method for producing a composite material for absorbent articles, whereby a substrate material and a water absorbent material can be composited together without using an adhesive, without heating, and without embedding the water absorbent material in the substrate material, is further provided.

DESCRIPTION OF EMBODIMENTS

Figure 1A:
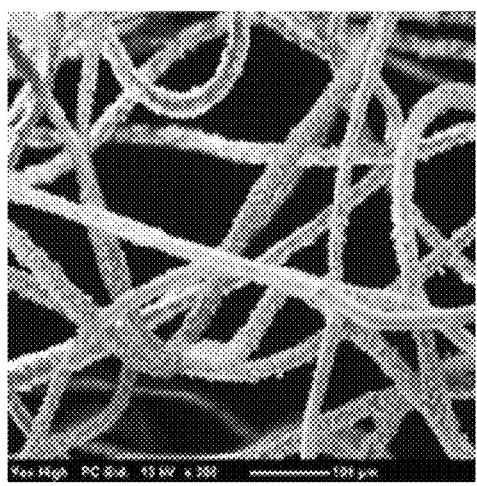
FIGS. 1(A) and (B) are electron micrographs for a particle-composited, nonwoven fabric obtained in the Example (A is at a magnification of 300×, B is at a magnification of 600×).

The present invention will be described below in detail.

The present invention relates to a composite material for an absorbent article, comprising a substrate material having a surface which is positively or negatively electrostatically charged in a predetermined solvent selected from a non-polar organic solvent, a polar organic solvent, and a mixed solvent of a polar organic solvent and water, and a water absorbent material adsorbed thereon by electrostatic interaction, having a surface which is electrostatically charged to an electric charge opposite to that of the surface of the substrate material, wherein the substrate material comprises a fibrous base material or resinous base material and a polyelectrolyte layer provided in a surface layer thereof, and/or, the water absorbent material has a water absorbent particulate base material or water absorbent fibrous base material and a polyelectrolyte layer provided in a surface layer thereof.

The present invention further provides a method for producing a composite material for an absorbent article, comprising an adsorption step in which, in a predetermined solvent selected from a non-polar organic solvent, a polar organic solvent, and a mixed solvent of a polar organic solvent and water, a substrate material having a surface which is positively or negatively electrostatically charged in the predetermined solvent is contacted with a water absorbent material having a surface which is electrostatically charged to an electric charge opposite to that of the surface of the substrate material to adsorb the water absorbent material onto the substrate material by electrostatic interaction, wherein the substrate material comprises a fibrous base material or resinous base material and a polyelectrolyte layer provided in a surface layer thereof, and/or, wherein the water absorbent material has a water absorbent particulate base material or water absorbent fibrous base material and a polyelectrolyte layer provided in a surface layer thereof.

Since at least one of the substrate material and water absorbent material has on the surface layer thereof a polyelectrolyte layer, it is possible to effectively adsorb the water absorbent material onto the substrate material by electrostatic interaction, and thereby the substrate material and water absorbent material can be effectively composited together. As long as one of the substrate material and water absorbent material has a polyelectrolyte layer on the surface layer thereof, the other may have or may not have a polyelectrolyte layer on the surface layer thereof. However, in view of effectively adsorbing the water absorbent material onto the substrate material by electrostatic interaction, it is preferable that both the substrate material and water absorbent material have on the surface layer thereof a polyelectrolyte layer.

The substrate material may comprise a fibrous base material or resinous base material as a base material. The fibrous base material included in the substrate material is preferably an aggregate of fibers, and the configuration of the aggregate of fibers includes, for example, a nonwoven fabric sheet. The resinous base material included in the substrate material is preferably a resin formed article, and the configuration of the resin formed article includes, for example, a resin sheet. When the base material of the substrate material is an aggregate of fibers, the substrate material may comprise, in addition to coated fibers having a polyelectrolyte layer on the surface layer thereof, fibers that do not have a polyelectrolyte layer on the surface layer thereof. Further, in the plurality of coated fibers included in the substrate material, the type of the polyelectrolyte layer in the surface layer of each coated fiber may be the same or different.

The water absorbent material may comprise as a base material a water absorbent particulate base material or water absorbent fibrous base material. The water absorbent particulate base material or water absorbent fibrous base material included in the water absorbent material is preferably a plurality of water absorbent particles or water absorbent fibers. When the base material of the water absorbent material is a plurality of water absorbent particles or water absorbent fibers, the water absorbent material may comprise, in addition to coated particles or coated fibers having a polyelectrolyte layer on the surface layer thereof, particles or fibers that do not have a polyelectrolyte layer on the surface layer thereof. Further, in the plurality of coated particles or coated fibers included in the water absorbent material, the type of the polyelectrolyte layer in the surface layer of each coated particle or each coated fiber may be the same or different.

The surface of the substrate material and the surface of the water absorbent material are electrostatically charged to electric charges opposite to each other in the predetermined solvent. The electric charge of the surface of a material having a polyelectrolyte layer in the surface layer thereof is determined by the electric charge of the polyelectrolyte layer located in the surface layer. For example, a material having in the surface layer thereof a polyelectrolyte layer which is positively electrostatically charged in a predetermined solvent is a material the surface of which is positively electrostatically charged in the predetermined solvent, and a material having a polyelectrolyte layer which is negatively electrostatically charged in a predetermined solvent is a material the surface of which is negatively electrostatically charged in the predetermined solvent.

The absolute values of the zeta potentials of the substrate material and water absorbent material in a predetermined solvent are preferably 20 mV or more, and more preferably 50 mV or more. In other words, the zeta potential when electrostatically positively charged is preferably +20 mV or more, and more preferably +50 mV or more, and the zeta potential when electrostatically negatively charged is preferably −20 mV or less, and more preferably −50 mV or less. Further, the absolute values of the zeta potentials of the substrate material and water absorbent material in a predetermined solvent are preferably balanced in charge. As used herein, "balanced in charge" means that the absolute values of the zeta potentials of the substrate material and water absorbent material are equal to or substantially equal to each other, and "the absolute values are substantially equal to each other" means that the difference between the absolute value of the zeta potential of the substrate material and the absolute value of the zeta potential of the water absorbent material (the difference determined by subtracting the smaller absolute value from the larger absolute value) is 20% or less, preferably 15% or less, and more preferably 10% or less based on the larger absolute value. The upper limit of the zeta potential is typically +100 mV, and preferably +70 mV, when positively electrostatically charged, and the upper limit of the zeta potential is typically −100 mV, and preferably −70 mV, when negatively electrostatically charged.

The zeta potentials of the substrate material and water absorbent material are measured under ambient atmosphere at 20° C. using a zeta potential measurement system ELSZ-1 manufactured by Otsuka Electronics. Under these circumstances, in the measurement of a zeta potential of particles, the mode is for the measurement using a flow cell, and the measurement principle utilizes a laser Doppler method (electrophoretic light scattering measurement method). Further, in the measurement of a zeta potential of fibers, the mode is for the measurement using a flat plate sample cell, and the measurement principle utilizes an electroosmotic flow generated in a liquid in contact with a sample surface.

A coated material comprising a base material (fibrous base material or resinous base material) and one or more polyelectrolyte layers covering the base material, one of the one or more polyelectrolyte layers is located in the surface layer, can be used as the substrate material. Preferably, the coated material used as the substrate material has a plurality of polyelectrolyte layers stacked together, and, in the plurality of polyelectrolyte layers, polyelectrolyte layers that are electrostatically charged to electric charges opposite to each other in the predetermined solvent are adjacent to each other. Although the number of polyelectrolyte layers of the coated material is not particularly limited, this number is preferably adjusted so that the absolute value of the zeta potential of a predetermined solvent is 20 mV or more (i.e., +20 mV or more when positively electrostatically charged, and −20 mV or less when negatively charged), and more preferably 50 mV or more (i.e., +50 mV or more when positively charged, and −50 mV or less when negatively electrostatically charged). Further, the number of polyelectrolyte layers of the coated material is preferably adjusted so that the absolute values of the zeta potentials of the substrate material and water absorbent material are balanced in charge. As used herein, "balanced in charge" means that the absolute values of the zeta potentials of the substrate material and water absorbent material are equal to or substantially equal to each other, and "the absolute values are substantially equal to each other" means that the difference between the absolute value of the zeta potential of the substrate material and the absolute value of the zeta potential of the water absorbent material (the difference determined by subtracting the smaller absolute value from the larger absolute value) is 20% or less, preferably 15% or less, and more preferably 10% or less based on the larger absolute value. The upper limit of the zeta potential of the coated material is typically +100 mV, and preferably +70 mV, when positively electrostatically charged, and the upper limit of the zeta potential of the coated material is typically −100 mV, and preferably −70 mV, when negatively electrostatically charged.

A coated material having a base material (water absorbent particulate base material or water absorbent fibrous base material) and one or more polyelectrolyte layers covering the base material, one of the one or more polyelectrolyte layers is located in a surface layer thereof, can be used as the water absorbent material. Preferably, the coated material used as the water absorbent material has a plurality of polyelectrolyte layers stacked together, and in the plurality of polyelectrolyte layers, polyelectrolyte layers that are electrostatically charged to electric charges opposite to each other in the predetermined solvent are adjacent to each other. Although the number of polyelectrolyte layers of the coated material is not particularly limited, this number is preferably adjusted so that the absolute value of the zeta potential of a predetermined solvent is 20 mV or more (i.e., +20 mV or more when positively electrostatically charged, and −20 mV or less when negatively electrostatically charged), and more preferably 50 mV or more (i.e., +50 mV or more when positively electrostatically charged, and −50 mV or less when negatively electrostatically charged). Further, the number of polyelectrolyte layers of the coated material is preferably adjusted so that the absolute values of the zeta potentials of the substrate material and water absorbent material are balanced in charge. As used herein, "balanced in charge" means that the absolute values of the zeta potentials of the substrate material and water absorbent material are equal to or substantially equal to each other, and "the absolute values are substantially equal to each other" means that the difference between the absolute value of the zeta potential of the substrate material and the absolute value of the zeta potential of the water absorbent material (the difference determined by subtracting the smaller absolute value from the larger absolute value) is 20% or less, preferably 15% or less, and more preferably 10% or less based on the larger absolute value. The upper limit of the zeta potential of the coated material is typically +100 mV, and preferably +70 mV, when positively electrostatically charged, and the upper limit of the zeta potential of the coated material is typically −100 mV, and preferably −70 mV, when negatively electrostatically charged.

Since the composite material of the present invention can be produced by a method comprising an adsorption step in which, in a predetermined solvent selected from a non-polar organic solvent, a polar organic solvent, and a mixed solvent of a polar organic solvent and water, a substrate material having a surface which is positively or negatively electrostatically charged in the predetermined solvent is contacted with a water absorbent material having a surface which is electrostatically charged to an electric charge opposite to that of the surface of the substrate material to adsorb the water absorbent material onto the substrate material by electrostatic interaction, the substrate material and water absorbent material can be composited together without an adhesive, without heating, and without the water absorbent material being embedded in the substrate material.

In the adsorption step, a predetermined solvent selected from a non-polar organic solvent, a polar organic solvent, and a mixed solvent of a polar organic solvent and water, is used. The types of the non-polar organic solvent and polar organic solvent are not particularly limited as long as the polyelectrolyte can ionize. Although typical polyelectrolytes can ionize in a polar solvent, there also exist polyelectrolytes designed to ionize in a non-polar solvent (e.g., ACS Macro Lett. 2012, 1, 1270-1273). When the polyelectrolyte ionizes in a polar solvent, the solvent used in the adsorption step is a mixed solvent of a polar organic solvent or polar solvent and water, and when the polyelectrolyte ionizes in a non-polar solvent, the solvent used in the adsorption step is a non-polar organic solvent. Since the organic solvent can be readily volatilized, the composite material produced by the adsorption step can be readily dried by natural drying or with a small heating amount when a dryer is used. Accordingly, it is possible to prevent a change in structure and properties of the substrate material and water absorbent material that may occur in the drying process performed after the adsorption step. For example, when the water absorbent material is particles containing a superabsorbent resin (Superabsorbent Polymer: SAP), it is possible to prevent the SAP from crosslinking due to heating and from decreasing in the water absorbing performance caused thereby, and it is also possible to prevent the water absorbent material from embedding in the substrate material due to heating and to prevent the SAP from decreasing in the water absorbing performance caused thereby.

The polar organic solvent used for the polyelectrolyte which ionizes in a polar solvent includes, for example, monohydric alcohols, polyhydric alcohols, ketones, and the like. Monohydric alcohols include, for example, methanol, ethanol, propyl alcohol, isopropyl alcohol, and the like, and ketones include, for example, acetone, ethyl methyl ketone, diethyl ketone, and the like.

The polar organic solvent is preferably an alcohol, and more preferably a monohydric alcohol having 1 to 3 carbon atoms.

The proportion of the polar organic solvent in the mixed solvent of the polar organic solvent and water is not particularly limited. However, when the water absorbent material has a water absorbent particulate base material or water absorbent fibrous base material and a polyelectrolyte layer provided in the surface layer thereof, the higher the proportion of an organic solvent, the less the water absorption by the water absorbent material in the adsorption step, and accordingly the time required for drying the composite material produced through the adsorption step, heating amount, etc., can be decreased. Therefore, the proportion of the organic solvent in the mixed solvent is preferably as high as possible. The proportion of the organic solvent in the mixed solvent is typically 95.0 wt % or more, preferably 97.0 wt % or more, and more preferably 99.5 wt % or more. The water contained in the mixed solvent of the polar organic solvent and water includes, for example, tap water, ion exchange water, distilled water, and the like, and is preferably ion exchange water.

The non-polar organic solvent used in the polyelectrolyte which ionizes in a non-polar solvent includes, for example, methylene chloride, tetrahydrofuran, ethyl acetate, chloroform, diethyl ether, toluene, benzene, hexane, and the like.

When the substrate material and the water absorbent material are contacted with each other in a solvent in the adsorption step, the contact time is typically from 1 to 60 minutes, preferably from 3 to 20 minutes, and more preferably from 5 to 15 minutes, the temperature of the solvent is typically from 0 to 50° C., preferably from 10 to 40° C., and more preferably from 20 to 30° C., and the pH of the solvent is typically from 4 to 10, preferably from 5 to 9, and more preferably from 6 to 8. When the water absorbent material is particles (i.e., coated particles having a water absorbent particulate substrate and a polyelectrolyte layer provided in the surface layer thereof), the concentration of the particles in the solvent when the substrate material and the water absorbent material are contacted with each other in a solvent is typically from 0.1 to 20 vol %, preferably from 0.2 to 10 vol %, and more preferably from 0.5 to 5 vol %.

A composite material in which the substrate material and water absorbent material are composited together can be produced by adsorbing the water absorbent material on the substrate material by electrostatic interaction in the adsorption step. After the adsorption step, a drying step may be performed to dry the composite material. The drying step is not particularly limited as long as the organic solvent can be volatilized, and the drying step may be natural drying or may be drying by a dryer. In the case of drying by a dryer, the drying temperature is needed to be lower than the melting points of the substrate material and water absorbent material. If the melting points of the base material and water-absorbent material are more than 100° C., it is typically from 30 to 100° C., preferably from 40 to 90° C., and more preferably from 50 to 80° C. The drying time can be adjusted appropriately depending on the drying temperature, and is typically from 1 to 30 minutes, preferably from 5 to 25 minutes, and more preferably from 10 to 20 minutes.

A coated material having a base material (fibrous base material or resinous base material) and one polyelectrolyte layer covering the base material, can be produced by step ($a_1$) below, and the coated material thus produced can be used as the substrate material or a material for the substrate material in the adsorption step. A coated material having a base material (fibrous base material or resinous base material) and 2 or more polyelectrolyte layers covering the base material can be produced by steps ($a_1$) to ($c_1$) below, and the coated material (the second or the (m+1)-th covered body) thus produced can be used as the substrate material in the adsorption step:

($a_1$) contacting, in a predetermined solvent selected from water, a non-polar organic solvent, a polar organic solvent, and a mixed solvent of a polar organic solvent and water, a fibrous base material or resinous base material having a surface which is positively or negatively electrostatically charged in the predetermined solvent with a polyelectrolyte which is electrostatically charged to an electric charge opposite to that of the surface of the fibrous base material or resinous base material in the predetermined solvent to produce a first coated material having in a surface layer thereof a first polyelectrolyte layer;

($b_1$) contacting, in a predetermined solvent selected from water, a non-polar organic solvent, a polar organic solvent, and a mixed solvent of a polar organic solvent and water, a $k_1$-th coated material, wherein $k_1$ is an integer of 1 or more, having in a surface layer thereof a $k_1$-th polyelectrolyte layer which is positively or negatively electrostatically charged in the predetermined solvent with a polyelectrolyte which is electrostatically charged to an electric charge opposite to that of the $k_1$-th polyelectrolyte layer in the predetermined solvent to produce a ($k_1$+1)-th coated material having in a surface layer thereof a ($k_1$+1)-th polyelectrolyte layer, and ($c_1$) performing step ($b_1$) at $k_1$=1 to produce a second coated material having in a surface layer thereof a second polyelectrolyte layer, or performing step ($b_1$) repeatedly from $k_1$=1 to $k_1$=m, wherein m is an integer of 2 or more, to produce a (m+1)-th coated material having in a surface thereof a (m+1)-th polyelectrolyte layer.

Steps ($a_1$) to ($c_1$) will be described below.
<Step ($a_1$)>

The base material (fibrous base material or resinous base material) having a surface which is positively electrostatically charged in a predetermined solvent is not particularly limited as long as it has a cationic group on the surface thereof. The cationic group is a group which ionizes in a predetermined solvent to have a positive electrostatic charge, and includes, for example, primary amino group, secondary amino group, tertiary amino group, quaternary ammonium group, quaternary phosphonium group, sulfonium group, pyridinium group, and the like. The cationic group may be a group which the base material originally has or may be a group which is artificially introduced. The base material having a surface which is positively electrostatically charged in a predetermined solvent may have some anionic groups on the surface thereof as long as the surface is positively electrostatically charged as a whole.

The base material (fibrous base material or resinous base material) having a surface which is electrostatically negatively charged in a predetermined solvent is not particularly limited as long as it has an anionic group on the surface thereof. The anionic group is a group which ionizes in a predetermined solvent to have a negative electrostatic charge, and includes, for example, hydroxyl group, carboxyl group, sulfonic acid group, sulfinic acid group, phosphoric acid group, and the like. The anionic group may be a group which the base material originally has or may be a group which is artificially introduced. The base material having a surface which is negatively electrostatically charged in a predetermined solvent may have some cationic groups on the surface thereof as long as the surface is negatively electrostatically charged as a whole.

The surface modification (introduction of a cationic group or anionic group) of the base material (fibrous base material or resinous base material) may be performed in accordance with a conventional method.

The types of the fibers that constitute the fibrous base material are not particularly limited, and specific examples thereof include natural fibers (wool, cotton, etc.), regenerated fibers (rayon, acetate, etc.), inorganic fibers (glass fibers, carbon fibers, etc.), thermoplastic resin fibers (polyolefins such as polyethylene, polypropylene, polybutylene, ethylene-vinyl acetate copolymer, ethylene-ethyl acrylate copolymer, ethylene-acrylic acid copolymer, and ionomer resins; polyesters such as polyethylene terephthalate, polybutylene terephthalate, polytrimethylene terephthalate, and polylactic acid; and polyamides such as nylon), and surface-modified derivatives, etc. The fibers are preferably thermoplastic resin fibers or surface-modified derivatives thereof.

The fibers that constitute the fibrous base material may be any of single component fibers; composite fibers such as core-sheath type fibers, side-by-side type fibers, and island/sea type fibers; hollow type fibers; profiled fibers such as those of flat type, Y-shaped type, and C-shaped type; latent crimping or actually crimped three-dimensional crimp fibers; splittable fibers capable of being split by a physical load such as water stream, heat, embossing, etc.

The average fiber diameter of the fibrous base material is typically from 10 to 40 μm, preferably from 12 to 38 μm, and more preferably from 14 to 36 μm. The average fiber diameter as described herein is the average fiber diameter as measured by the following method. The base material fibers are magnified 300 times by an electron microscope (VE-8800 manufactured by Keyence Corporation), and a distance between two points on a fiber in a magnified image is measured. The same measurements are performed on arbitrary 30 fibers (n=30), and the average value thereof is taken as an average fiber diameter. When only a few (e.g., 3 to 5) fibers are displayed in a magnified image, several magnified images are taken with changing the region of the fibrous base material to be magnified by the electron microscope to achieve n=30.

The type of the resin which constitutes the resinous base material is not particularly limited, and specific examples thereof include polyolefins, polyesters, polyamides, and the like. Polyolefins include, for example, linear low density polyethylene (LLDPE), low density polyethylene (LDPE), medium density polyethylene (MDPE), high density polyethylene (HDPE), polypropylene, polybutylene, copolymers comprising mainly of these components (e.g., ethylene-vinyl acetate copolymer (EVA), ethylene-ethyl acrylate copolymer (EEA), ethylene-acrylic acid copolymer (EAA), ionomer resins), and the like. Polyesters include, for example, polyesters of a linear or branched chain polyhydroxy alkanoic acid having carbon atoms of up to 20, including polyethylene terephthalate (PET), polytrimethylene terephthalate (PTT), polybutylene terephthalate (PBT), polylactic acid, polyglycolic acid, and the like, and copolymers comprising mainly of these polyesters, or copolymerized polyesters formed by copolymerizing as a main component an alkylene terephthalate with a minor amount of other components. Polyamides include, for example, 6-Nylon, 6,6-Nylon, and the like. A resin formed article formed in accordance with a conventional method can be used as a resinous base material.

In step ($a_1$), if a base material having a surface which is positively electrostatically charged in a predetermined solvent is used, a polyelectrolyte which is negatively electrostatically charged in the predetermined solvent is used. The polyelectrolyte which is negatively electrostatically charged in the predetermined solvent includes, for example, anionic polymers such as polystyrene sulfonic acid (PSS), polyvinyl sulfate (PVS), polyacrylic acid (PAA), polymethacrylic acid (PMA), and polycarboxylic acid (PCA).

In step ($a_1$), if a base material having a surface which is negatively electrostatically charged in a predetermined solvent is used, a polyelectrolyte which is positively electrostatically charged in the predetermined solvent is used. The polyelectrolyte which is positively electrostatically charged in the predetermined solvent includes, for example, poly (diallyl dimethyl ammonium chloride) (PDDA), polyethyleneimine (PEI), polyvinylamine (PVAm), poly (vinyl pyrrolidone/N,N-dimethylaminoethyl acrylate) copolymer, and the like.

The predetermined solvent selected from water, a non-polar organic solvent, a polar organic solvent, and a mixed solvent of a polar organic solvent and water is not particularly limited as long as the polyelectrolyte can ionize. When the polyelectrolyte ionizes in a polar solvent, the solvent used in step ($a_1$) is water, a polar organic solvent, or a mixed solvent of a polar organic solvent and water, and when the polyelectrolyte ionizes in a non-polar solvent, the solvent used in step ($a_1$) is a non-polar organic solvent. The water includes, for example, tap water, ion exchange water, distilled water, and the like, and is preferably ion exchange water. The specific examples of the polar organic solvent and non-polar organic solvent are the same as for the adsorption step.

When the base material and the polyelectrolyte are contacted with each other in a predetermined solvent, the concentration of the polyelectrolyte in the solvent is typically from 0.05 to 10 wt %, preferably from 0.1 to 5 wt %, and more preferably from 0.2 to 1 wt %, the contact time is typically from 1 to 60 minutes, preferably from 3 to 20 minutes, and more preferably from 5 to 15 minutes, the temperature of the solvent is typically from 0 to 50° C., preferably from 10 to 40° C., and more preferably from 20 to 30° C., and the pH of the solvent is typically from 4 to 10, preferably from 5 to 9, and more preferably from 6 to 8.

In one embodiment of step ($a_1$), a first coated material in which a base material which is positively electrostatically charged is coated with a polyelectrolyte layer which is negatively electrostatically charged can be produced by contacting in a predetermined solvent a base material having a surface which is positively electrostatically charged in the predetermined solvent with a polyelectrolyte which is negatively electrostatically charged in the predetermined solvent. In another embodiment of step ($a_1$), a first coated material in which a base material which is negatively electrostatically charged is coated with a polyelectrolyte layer which is positively electrostatically charged can be produced by contacting in a predetermined solvent a base material having a surface which is negatively electrostatically charged in the predetermined solvent with a polyelectrolyte which is positively electrostatically charged in the predetermined solvent.

After step ($a_1$), a washing step is preferably performed to wash the first coated material with an organic solvent, thereby removing an excess polyelectrolyte adhered to the first coated material. After the washing step, a drying step may be carried out to dry the first coated material. The drying step is not particularly limited as long as the organic solvent can be volatilized, and may be natural drying or may be drying by a dryer.

<Step ($b_1$)>

In one embodiment of step ($b_1$), contacting, in a predetermined solvent, a $k_1$-th coated material having in a surface layer thereof a $k_1$-th polyelectrolyte layer which is positively electrostatically charged in the predetermined solvent with a polyelectrolyte which is negatively electrostatically charged in the predetermined solvent produces a ($k_1$+1)-th coated material having in a surface layer thereof a ($k_1$+1)-th polyelectrolyte layer which is negatively charged in the predetermined solvent.

In another embodiment of step ($b_1$), contacting, in a predetermined solvent, a $k_1$-th coated material having in a surface layer thereof a $k_1$-th polyelectrolyte layer which is negatively electrostatically charged in the predetermined solvent with a polyelectrolyte which is positively electrostatically charged in the predetermined solvent produces a ($k_1$+1)-th coated material having in a surface layer thereof a ($k_1$+1)-th polyelectrolyte layer which is positively charged in the predetermined solvent.

Specific examples of the polyelectrolyte, specific examples of the predetermined solvent, the conditions of contacting the $k_1$-th coated material and the polyelectrolyte, etc., are the same as for step ($a_1$).

<Step ($c_1$)>

A second coated material having a base material as well as the first and second polyelectrolyte layers covering the base material, wherein the second polyelectrolyte layer being located in a surface layer thereof, can be produced by performing step ($b_1$) at $k_1$=1. A (m+1)-th coated material having a base material as well as the first to (m+1)-th polyelectrolyte layers covering the base material, wherein the (m+1)-th polyelectrolyte layer being located in a surface layer thereof, can be produced by performing step ($b_1$) repeatedly from $k_1$=1 to $k_1$=m, wherein m is an integer of 2 or more. The first to (m+1)-th polyelectrolyte layers are stacked together so that polyelectrolyte layers that are electrostatically charged to electric charges opposite to each other in the predetermined solvent are adjacent to each other. For example, when a base material having a surface which is positively electrostatically charged in a predetermined solvent is used, if m is 3, a negatively electrostatically charged first polyelectrolyte layer, a positively electrostatically charged second polyelectrolyte layer, a negatively electrostatically charged third polyelectrolyte layer, and a positively electrostatically charged fourth polyelectrolyte layer are stacked on a base material, thereby producing a fourth coated material having the fourth polyelectrolyte layer in a surface layer thereof. Further, when a base material having a surface which is negatively electrostatically charged in a predetermined solvent is used, if m is 3, a positively electrostatically charged first polyelectrolyte layer, a negatively electrostatically charged second polyelectrolyte layer, a positively electrostatically charged third polyelectrolyte layer, and a negatively electrostatically charged fourth polyelectrolyte layer are stacked on a base material, thereby producing a fourth coated material having the fourth polyelectrolyte layer in a surface layer thereof.

Although m is not particularly limited as long as it is an integer of 2 or more, m is preferably from 2 to 5, and more preferably from 3 to 4. This makes the polyelectrolyte layers to have a constant the charge density and increases the strength thereof, thereby achieving a uniform surface coverage.

Incidentally, m is adjusted so that the (m+1)-th polyelectrolyte layer located in the surface layer of the coated material is electrostatically charged to an electric charge opposite to that of the surface of the water absorbent material to be contacted with the (m+1)-th coated material in the adsorption step.

In one embodiment of step $(a_1)$ to $(c_1)$, a base material having a surface which is positively electrostatically charged in a predetermined solvent is immersed in an anionic polymer solution and a cationic polymer solution, alternately, thereby producing a coated material in which anionic and cationic polymer layers are stacked on the base material.

In another embodiment of step $(a_1)$ to $(c_1)$, a base material having a surface which is negatively electrostatically charged in a predetermined solvent is immersed in a cationic polymer solution and an anionic polymer solution, alternately, thereby producing a coated material in which cationic and anionic polymer layers are stacked on the base material.

A coated material having a base material (water absorbent particulate base material or water absorbent fibrous base material) and one polyelectrolyte layer covering the base material can be produced by step $(a_2)$ described below, and the resulting coated material can be used as a water absorbent material in the adsorption step. A coated material (water absorbent particulate base material or water absorbent fibrous base material) having a base material and two or more polyelectrolyte layers covering the base material can be produced by steps $(a_2)$ to $(c_2)$ described below, and the resulting coated material (the second or (n+1)-th coated material) can be used as a water absorbent material in the adsorption step:

$(a_2)$ contacting, in a predetermined solvent selected from a non-polar organic solvent, a polar organic solvent, and a mixed solvent of a polar organic solvent and water, a water absorbent particulate base material or water absorbent fibrous base material having a surface which is positively or negatively electrostatically charged in the predetermined solvent with a polyelectrolyte which is electrostatically charged to an electric charge opposite to that of the surface of the water absorbent particulate base material or water absorbent fibrous base material in the predetermined solvent to produce a first coated material having in a surface layer thereof a first polyelectrolyte layer;

$(b_2)$ contacting, in a predetermined solvent selected from a non-polar organic solvent, a polar organic solvent, and a mixed solvent of a polar organic solvent and water, a $k_2$-th coated material, wherein $k_2$ is an integer of 1 or more, having in a surface layer thereof a $k_2$-th polyelectrolyte layer which is positively or negatively electrostatically charged in the predetermined solvent with a polyelectrolyte which is electrostatically charged to an electric charge opposite to that of the $k_1$-th polyelectrolyte layer in the predetermined solvent to produce a $(k_2+1)$-th coated material having in a surface layer thereof a $(k_2+1)$-th polyelectrolyte layer; and $(c_2)$ performing step $(b_2)$ at $k_2=1$ to produce a second coated material having in a surface layer thereof a second polyelectrolyte layer, or performing step $(b_2)$ repeatedly from $k_2=1$ to $k_2=n$, wherein n is an integer of 2 or more, to produce a (n+1)-th coated material having in a surface layer thereof a (n+1)-th polyelectrolyte layer.

Steps $(a_2)$ to $(c_2)$ will be described below.

<Step $(a_2)$>

The base material (water absorbent particulate base material or water absorbent fibrous base material) having a surface which is positively electrostatically charged in a predetermined solvent is not particularly limited as long as it has a cationic group on the surface thereof. The cationic group is a group which ionizes in a predetermined solvent to have a positive electrostatic charge, and includes, for example, primary amino group, secondary amino group, tertiary amino group, quaternary ammonium group, quaternary phosphonium group, sulfonium group, pyridinium group, and the like. The cationic group may be a group which the base material originally has or may be a group which is artificially introduced. The base material having a surface which is positively electrostatically charged in a predetermined solvent may have some anionic groups on the surface thereof as long as the surface is positively electrostatically charged as a whole.

The base material (water absorbent particulate base material or water absorbent fibrous base material) having a surface which is electrostatically negatively charged in a predetermined solvent is not particularly limited as long as it has an anionic group on the surface thereof. The anionic group is a group which ionizes in a predetermined solvent to have a negative electrostatic charge, and includes, for example, hydroxyl group, carboxyl group, sulfonic acid group, sulfinic acid group, phosphoric acid group, and the like. The anionic group may be a group which the base material originally has or may be a group which is artificially introduced. The base material having a surface which is positively electrostatically charged in a predetermined solvent may have some cationic groups on the surface thereof as long as the surface is negatively electrostatically charged as a whole.

The surface modification (introduction of a cationic group or anionic group) of the base material (water absorbent particulate base material or water absorbent fibrous base material) may be performed in accordance with a conventional method.

The water absorbent particulate base material includes, for example, particles containing a superabsorbent resin (Superabsorbent Polymer: SAP) or surface-modified derivatives thereof. The superabsorbent resin includes, for example, starch-based, cellulose-based, and synthetic polymer-based superabsorbent resins. The starch-based or cellulose-based superabsorbent resins include, for example, starch-acrylic acid (salt) graft copolymers, saponified products of starch-acrylonitrile copolymers, crosslinked products of sodium carboxymethylcellulose, and the like, and the synthetic polymer-based, superabsorbent material include, for example, polyacrylic acid salt-based, polysulfonic acid salt-based, maleic anhydride salt-based, polyacrylamide-based polyvinyl alcohol-based, polyethylene oxide-based, polyaspartic acid salt-based, polyglutamic acid-based, polyalginic acid salt-based, starch-based, and cellulose-based superabsorbent resins, and among these, polyacrylic acid salt-based (particularly sodium polyacrylate-based) superabsorbent resins are preferred.

The average particle diameter of the water absorbent particulate base material is typically from 200 nm to 20 µm, preferably from 1 µm to 15 µm, and more preferably from 3 µm to 10 µm. Further, in view of the dispersibility in solvent in the surface charging step, the average particle diameter of the water absorbent particulate base material is preferably about 5 µm. Further, when the substrate material comprises a fibrous base material, the average particle diameter of the water absorbent particulate base material is preferably smaller than the average fiber diameter of the fibrous base material included in the substrate material. The measurement of the particle diameter is implemented in accordance with the sieving test method described in JIS R 6002: 1998.

The fibers that constitute the water-absorbent fibrous base material are not particularly limited as long as they have water absorbing properties, and specific examples thereof include wood pulps (e.g., mechanical pulps such as ground pulp, refiner ground pulp, thermomechanical pulp, and chemi-thermomechanical pulp; chemical pulps such as kraft pulp, sulfide pulp, and alkaline pulp; semichemical pulp, etc.) obtained from softwood or hardwood as a raw material; mercerized pulp obtained by subjecting a wood pulp to a chemical treatment or crosslinked pulp; non-wood pulps such as bagasse, kenaf, bamboo, hemp, and cotton (for example, cotton linters); regenerated fibers such as rayon and fibrillated rayon; semi-synthetic cellulose such as acetate and triacetate, and the like.

The fibers that constitute the water absorbent fibrous base material may be any of single component fibers; composite fibers such as core-sheath type fibers, side-by-side type fibers, and island/sea type fibers; hollow type fibers; profiled fibers such as those of flat type, Y-shaped type, and C-shaped type; latent crimping or actually crimped three-dimensional crimp fibers; splittable fibers capable of being split by a physical load such as water stream, heat, embossing, etc.

When the substrate material comprises a fibrous base material, the length of the water absorbent fibrous base material is preferably shorter than the length of the fibrous base material included in the substrate material. The average fiber diameter of the water absorbent fibrous base material is typically from 10 to 40 µm, preferably from 12 to 38 µm, and more preferably from 14 to 36 µm. The average fiber diameter described herein is the average fiber diameter as measured by the same method as described above.

Specific examples of the polyelectrolyte, specific examples of the predetermined solvent, the conditions for contacting the base material particles and the polyelectrolyte in the predetermined solvent, etc., are the same as step $(a_1)$. The predetermined solvent used in step $(a_1)$ is selected from water, a non-polar organic solvent, a polar organic solvent, and a mixed solvent of a polar organic solvent and water, whereas the predetermined solvent used in step $(a_2)$ is selected from a non-polar organic solvent, a polar organic solvent, and a mixed solvent of a polar organic solvent and water.

In one embodiment of step $(a_2)$, a first coated material in which a base material which is positively electrostatically charged is coated with a polyelectrolyte layer which is negatively electrostatically charged can be produced by contacting in a predetermined solvent a base material having a surface which is positively electrostatically charged in the predetermined solvent with a polyelectrolyte which is negatively electrostatically charged in the predetermined solvent. In another embodiment of step $(a_2)$, a first coated material in which a base material which is negatively electrostatically charged is coated with a polyelectrolyte layer which is positively electrostatically charged can be produced by contacting in a predetermined solvent a base material having a surface which is negatively electrostatically charged in the predetermined solvent with a polyelectrolyte which is positively electrostatically charged in the predetermined solvent.

After step $(a_2)$, a washing step is preferably performed to wash the first coated material with an organic solvent, thereby removing an excess polyelectrolyte adhered to the first coated material. After the washing step, a drying step may be carried out to dry the first coated material. The drying step is not particularly limited as long as the organic solvent can be volatilized, and may be natural drying or may be drying by a dryer.

<Step $(b_2)$>

In one embodiment of step $(b_2)$, contacting, in a predetermined solvent, a $k_2$-th coated material having in a surface layer thereof a $k_1$-th polyelectrolyte layer which is positively electrostatically charged in the predetermined solvent with a polyelectrolyte which is negatively electrostatically charged in the predetermined solvent produces a $(k_2+1)$-th coated material having in a surface layer thereof a $(k_2+1)$-th polyelectrolyte layer which is negatively charged in the predetermined solvent.

In another embodiment of step $(b_2)$, contacting, in a predetermined solvent, a $k_2$-th coated material having in a surface layer thereof a $k_2$-th polyelectrolyte layer which is negatively electrostatically charged in the predetermined solvent with a polyelectrolyte which is positively electrostatically charged in the predetermined solvent produces a $(k_2+1)$-th coated material having in a surface layer thereof a $(k_2+1)$-th polyelectrolyte layer which is positively charged in the predetermined solvent.

Specific examples of the polyelectrolyte, specific examples of the predetermined solvent, the conditions for contacting the $k_2$-th coated material and the polyelectrolyte in the predetermined solvent, etc., are the same as for step $(a_1)$. The predetermined solvent used in step $(a_1)$ is selected from water, a non-polar organic solvent, a polar organic solvent, and a mixed solvent of a polar organic solvent and water, whereas the predetermined solvent used in step $(b_2)$ is selected from a non-polar organic solvent, a polar organic solvent, and a mixed solvent of a polar organic solvent and water.

<Step $(c_2)$>

A second coated material having a base material as well as the first and second polyelectrolyte layers covering the base material, wherein the second polyelectrolyte layer being located in a surface layer thereof, can be produced by performing step $(b_2)$ at $k_2=1$. A $(n+1)$-th coated material having a base material as well as the first to $(n+1)$-th polyelectrolyte layers covering the base material, wherein the $(n+1)$-th polyelectrolyte layer being located in a surface layer thereof, can be produced by performing step $(b_2)$ repeatedly from $k_2=1$ to $k_2=n$, wherein n is an integer of 2 or more. The first to $(n+1)$-th polyelectrolyte layers are stacked together so that polyelectrolyte layers that are electrostatically charged to electric charges opposite to each other in the predetermined solvent are adjacent to each other. For example, when a base material having a surface which is positively electrostatically charged in a predetermined solvent is used, if n is 3, a negatively electrostatically charged first polyelectrolyte layer, a positively electrostatically charged second polyelectrolyte layer, a negatively electrostatically charged third polyelectrolyte layer, and a positively electrostatically charged fourth polyelectrolyte layer are stacked on a base material, thereby producing a fourth coated material having the fourth polyelectrolyte layer in a surface layer thereof. Further, when a base material having a surface which is negatively electrostatically charged in a predetermined solvent is used, if n is 3, a positively electrostatically charged first polyelectrolyte layer, a negatively electrostatically charged second polyelectrolyte layer, a positively electrostatically charged third polyelectrolyte layer, and a negatively electrostatically charged fourth polyelectrolyte layer are stacked on a base material, thereby producing a fourth coated material having the fourth polyelectrolyte layer in a surface layer thereof.

Although n is not particularly limited as long as it is an integer of 2 or more, n is preferably from 2 to 5, and more preferably from 2 to 3. This makes the polyelectrolyte layers to have a constant the charge density and increases the strength thereof, thereby achieving a uniform surface coverage.

Incidentally, n is adjusted so that the polyelectrolyte layer located in the surface layer of the coated material is electrostatically charged to an electric charge opposite to that of the surface of the substrate material to be contacted with the coated material in the adsorption step.

In one embodiment of step ($a_2$) to ($c_2$), a base material having a surface which is positively electrostatically charged in a predetermined solvent is immersed in an anionic polymer solution and a cationic polymer solution, alternately, thereby producing a coated material in which anionic and cationic polymer layers are stacked on the base material.

In another embodiment of step ($a_2$) to ($c_2$), a base material having a surface which is negatively electrostatically charged in a predetermined solvent is immersed in a cationic polymer solution and an anionic polymer solution, alternately, thereby producing a coated material in which cationic and anionic polymer layers are stacked on the base material.

The composite material of the present invention can be produced by compositing a substrate material and a water absorbent material together without using an adhesive, without heating particles, and without embedding the water absorbent material in the substrate material. The present invention is further directed to provide a method for producing a composite material for absorbent articles, whereby a substrate material and a water absorbent material can be composited together without using an adhesive, without heating particles, and without embedding the water absorbent material in the substrate material. Accordingly, a wide variety of materials can be applied as the substrate material and water absorbent material in the composite material of the present invention. For example, the composite material of the present invention is useful as a particle-composited fiber sheet having excellent water absorbing properties when fibers in the form of a nonwoven fabric is used as a substrate material, and a plurality of SAP particles are used as a water absorbent material (provided that one or both of the substrate material and water absorbent material has or have a polyelectrolyte layer provided in the surface layer thereof).

According to the method for producing a composite material for absorbent articles of the present invention, a composite material for absorbent articles can be produced by compositing a substrate material and a water absorbent material without using an adhesive, without heating, and without embedding the water absorbent material in the substrate material. Accordingly, the present invention is applicable to a wide variety of materials. For example, a particle-composited fiber sheet having excellent water absorbing properties can be produced when fibers in the form of a nonwoven fabric are used as a substrate material, and a plurality of SAP particles are used as a water absorbent material (provided that one or both of the substrate material and water absorbent material has or have a polyelectrolyte layer provided in the surface layer thereof).

The composite material of the present invention is used as a composite material for absorbent articles. The type and applications of the absorbent articles are not particularly limited. The absorbent article includes, for example, hygiene and sanitary articles such as disposable diapers, sanitary napkins, panty liners, incontinence liners, urine pads, breast pads, sweat sheets, and the like, and may be targeted to human, or animals other than human, such as pets. The liquid to be absorbed by the absorbent article is not particularly limited, and includes, for example, liquid excrements (e.g., menstrual blood, urine, body fluid, etc.) discharged from the wearer, etc. The composite material of the present invention can be used as one or more absorbent members of an absorbent article. For example, when an absorbent article comprises a liquid-permeable top sheet, a liquid-impermeable backsheet, and one or more absorbent members disposed between them, the composite material of the present invention can be used as the one or more absorbent members disposed between the liquid-permeable top sheet and the liquid-impermeable back sheet. When the composite material of the present invention is used as absorbent member disposed between a liquid-permeable top sheet and a liquid-impermeable backsheet, the composite material of the present invention is preferably in the form of a particle-composited fiber sheet obtained by using fibers in the form of a nonwoven fabric as a substrate material and using a plurality of SAP particle as a water absorbent material (provided that one or both of the substrate material and water absorbent material has or have a polyelectrolyte layer provided in the surface layer thereof). This makes it possible to produce an absorbent article which is thinner than conventional absorbent articles and is excellent in flexibility and gas-permeability.

EXAMPLES

Production Example 1

Production of Particle-Composited Synthetic Fiber Nonwoven Fabric

In this example, the following materials, reagents, conditions, etc., were used, unless otherwise specified.

Centrifugation was carried out using a centrifuge (manufacturer: Kubota Manufacturing Corporation, seller: Kubota Corporation, model: Universal Refrigerated Centrifuge 5922), and the centrifugation conditions are 8.5×g for 5 minutes.

As ethanol, an ethanol having a purity of 99.5%, manufactured by Wako Pure Chemical Industries, Ltd., was used.

As poly (diallyl dimethyl ammonium chloride) (hereinafter referred to as "PDDA"), a PDDA having a weight-average molecular weight (Mw) of from 100,000 to 200,000, manufactured by Aldrich Co., was used.

As polyacrylic acid (hereinafter referred to as "PAA"), PAA having a weight-average molecular weight (Mw) of from 25,000 to 50,000, manufactured by Aldrich, was used.

As SAP particles, SAP particles (trade name: SA55SX-II) manufactured by Sumitomo Seika Chemicals Co., Ltd., were used.

As nonwoven fabric, through-air, nonwoven fabric (basis weight: 38 g/m$^2$, thickness: 1.4 mm) composed of a core-sheath type composite fiber having PET as a core component and PE as a sheath component (4.4 dtex×38 mm) was used.

(1) Production of a Coated Nonwoven Fabric Coated with Polyelectrolyte Layers

Step $A_1$: The nonwoven fabric was charged in a container.

Step $B_1$: After step $A_1$, an amount of PAA solution in ethanol sufficient for the nonwoven fabric to be immersed therein was added and was allowed to stand for 15 minutes, and subsequently the PAA solution in ethanol was removed.

Step $C_1$: After step $B_1$, an amount of ethanol sufficient for the nonwoven fabric to be immersed therein was added and thoroughly shaken, and subsequently the ethanol was removed. This washing was repeated twice.

Step $D_1$: After step $C_1$, an amount of PDDA solution in ethanol sufficient for the nonwoven fabric to be immersed therein was added and was allowed to stand for 15 minutes, and subsequently the PDDA solution in ethanol was removed.

Step $E_1$: After step $D_1$, an amount of ethanol sufficient for the nonwoven fabric to be immersed therein was added and thoroughly shaken, and subsequently the ethanol was removed. This washing was repeated twice.

A coated nonwoven fabric in which a nonwoven fabric which is a base material is coated with a PAA layer and a PDDA layer and the PDDA layer is located in a surface layer was produced by steps $A_1$ to $E_1$.

The zeta potential of the coated nonwoven fabric in ethanol was measured with a zeta potential measurement system ELSZ-1 manufacture by Otsuka Electronics Co., Ltd., under ambient atmosphere at 20° C., and was determined to be +40 mV. In the measurement of the zeta potential of the coated nonwoven fabric, the mode is for the measurement using a flat plate sample cell, and the measurement principle utilizes an electroosmotic flow generated in a liquid in contact with a sample surface.

(2) Production of Coated SAP Particles Coated with Polyelectrolyte Layers

Step $A_2$: A 10 mL of ethanol and 0.5 g of SAP particles were added to a centrifuge tube attached to the centrifuge and were centrifuged, and the resulting supernatant was removed.

Step $B_2$: After step $A_2$, a 10 mL of PDDA solution in ethanol (PDDA concentration: 5 mg/mL) was added to the centrifuge tube and was allowed to stand for 15 minutes and centrifuged, and the resulting supernatant was removed.

Step $C_2$: After step $B_2$, a 10 mL of ethanol was added to a centrifuge tube and was thoroughly stirred and centrifuged, and the resulting supernatant was removed. This washing was repeated twice.

Step $D_2$: After step $C_2$, a 10 mL of PAA solution in ethanol (PAA concentration: 5 mg/mL) was added to the centrifuge tube and was allowed to stand for 15 minutes, and the resulting supernatant was removed.

Step $E_2$: After step $D_2$, a 10 mL of ethanol was added to the centrifuge tube and was thoroughly stirred and centrifuged, and the resulting supernatant was removed. This washing was repeated twice.

Coated SAP particles in which SAP particles that are a base material is coated with a PDDA layer and a PAA layer and the PAA layer is located in a surface layer were produced by steps $A_2$ to $E_2$.

The zeta potential of the coated SAP particles in ethanol was measured with a zeta potential measurement system ELSZ-1 manufacture by Otsuka Electronics Co., Ltd., under ambient atmosphere at 20° C., and was determined to be −40 mV. In the measurement of the zeta potential of the coated SAP particles, the mode is for the measurement using a flow cell, and the measurement principle utilizes a laser Doppler method (electrophoretic light scattering measurement method).

(3) Production of Composite Material

Composite materials (Samples 1 to 12) of the nonwoven fabric and SAP particles were produced by mixing the coated nonwoven fabric and coated SAP particles in ethanol, and adsorbing the coated SAP particles on the coated nonwoven fabric by electrostatic interaction.

The amounts of SAP particles composited, determined from the weights of the nonwoven fabric sheet before and after compositing SAP particles will be shown in Table 1.

TABLE 1

|  | Weight of nonwoven fabric sheet before compositing SAP particles (g) | Weight of nonwoven fabric sheet after compositing SAP particles (g) | SAP particles compositing amount (g) |
| --- | --- | --- | --- |
| Sample 1 | 0.3185 | 0.3337 | 0.0152 |
| Sample 2 | 0.2975 | 0.3132 | 0.0157 |
| Sample 3 | 0.2881 | 0.3025 | 0.0144 |
| Sample 4 | 0.2962 | 0.3119 | 0.0157 |
| Sample 5 | 0.2999 | 0.3123 | 0.0124 |
| Sample 6 | 0.2958 | 0.3126 | 0.0168 |
| Sample 7 | 0.3146 | 0.3365 | 0.0219 |
| Sample 8 | 0.2963 | 0.3103 | 0.0140 |
| Sample 9 | 0.3223 | 0.3427 | 0.0204 |
| Sample 10 | 0.2958 | 0.3235 | 0.0277 |
| Sample 11 | 0.2994 | 0.3212 | 0.0218 |
| Sample 12 | 0.3137 | 0.3492 | 0.0355 |

Test Example 1

Measurements for Water Absorption Ratio and Water Retention Ratio of SAP Particle-Composited Nonwoven Fabric A bag (x (g)) of 250-mesh nylon (N-NO. 250HD manufactured by NBC Industries) having an opening at the top end was charged with a sample (y (g)), and the top end was heat sealed. The sample-filled bag was completely immersed in a 0.9% physiological saline solution or ion exchange water and was allowed to stand for 60 minutes. After standing, the sample-filled bag was pulled up and was allowed to stand by itself for 25 minutes to drain water, and subsequently the weight ($z_1$ (g)) of the sample–filled bag was measured. A water absorption ratio (g/g) was calculated according to the following formula.

Water absorption ratio $(g/g) = (z_1 - x - y)/y$

After draining water by allowing to stand, the sample-filled bag was dewatered at 150 G for 90 seconds using the centrifuge, the weight ($z_2$ (g)) of the dewatered sample-filled bag was measured, and a water retention (g/g) was calculated according to the following formula.

Water retention ratio $(g/g) = (z_2 - x - y)/y$

The results are shown in Table 2. Incidentally, the water absorption ratio and water retention ratio are average values of water absorption ratios and water retention ratios calculated on Samples 2 and 3 in Table 1.

TABLE 2

|  | Ion exchange water | | Physiological saline solution | |
| --- | --- | --- | --- | --- |
|  | Water absorption ratio (g/g) | Water retention ratio (g/g) | Water absorption ratio (g/g) | Water retention ratio (g/g) |
| Nonwoven fabric sheet before compositing SAP | 16.11 | 10.39 | 15.84 | 11.08 |
| Nonwoven fabric sheet after compositing SAP | 38.63 | 16.95 | 21.16 | 11.14 |

As shown in Table 2, the water absorption ratio and water retention ratio were increased due to compositing SAP particles to a nonwoven fabric. Particularly, the water absorption ratio and water retention ratio for ion exchange water were significantly increased due to compositing SAP particles to a nonwoven fabric.

Figure 1B:
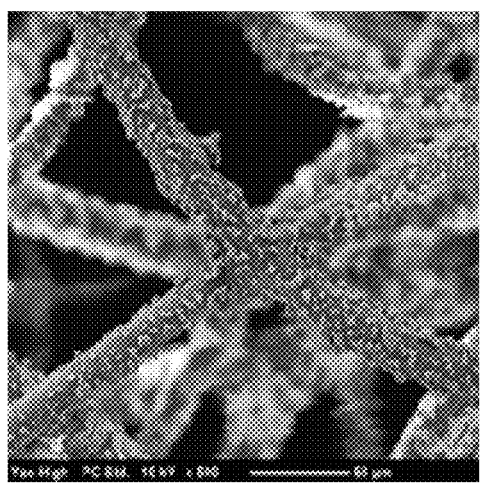

Further, as shown in FIG. 1, compositing of SAP particles to a nonwoven fabric was confirmed by observation (secondary electron imaging, accelerating voltage 10 kV) with electron microscope (JCM-5000 manufactured by JEOL). FIG. 1(A) is an electron micrograph at a magnification of 300×, and FIG. 1(B) is an electron micrograph at a magnification of 600×.

The invention claimed is:

1. A composite material for an absorbent article, comprising a substrate material having a surface which is positively or negatively electrostatically charged in a predetermined solvent selected from a non-polar organic solvent, a polar organic solvent, and a mixed solvent of a polar organic solvent and water, and a water absorbent material adsorbed thereon by electrostatic interaction, having a surface which is electrostatically charged to an electric charge opposite to that of the surface of the substrate material, wherein the substrate material comprises a fibrous base material or resinous base material and a polyelectrolyte layer provided in a surface layer thereof, and/or, the water absorbent material has a water absorbent particulate base material or water absorbent fibrous base material and a polyelectrolyte layer provided in a surface layer thereof.

2. The composite material according to claim 1, wherein the substrate material and/or the water absorbent material have a plurality of polyelectrolyte layers stacked together, and in the plurality of polyelectrolyte layers, polyelectrolyte layers that are electrostatically charged to electric charges opposite to each other in the predetermined solvent are adjacent to each other.

3. The composite material according to claim 1, wherein the substrate material and water absorbent material have a zeta potential of 20 mV or more in absolute value in the predetermined solvent, and are balanced in charge.

4. The composite material according to claim 1, wherein the substrate material is a second or (m+1)-th coated material produced by a method comprising the following steps $(a_1)$ to $(c_1)$:

($a_1$) contacting, in a predetermined solvent selected from water, a non-polar organic solvent, a polar organic solvent, and a mixed solvent of a polar organic solvent and water, a fibrous base material or resinous base material having a surface which is positively or negatively electrostatically charged in the predetermined solvent with a polyelectrolyte which is electrostatically charged to an electric charge opposite to that of the surface of the fibrous base material or resinous base material in the predetermined solvent to produce a first coated material having in a surface layer thereof a first polyelectrolyte layer;

($b_1$) contacting, in a predetermined solvent selected from water, a non-polar organic solvent, a polar organic solvent, and a mixed solvent of a polar organic solvent and water, a $k_1$-th coated material, wherein $k_1$ is an integer of 1 or more, having in a surface layer thereof a $k_1$-th polyelectrolyte layer which is positively or negatively electrostatically charged in the predetermined solvent with a polyelectrolyte which is electrostatically charged to an electric charge opposite to that of the $k_1$-th polyelectrolyte layer in the predetermined solvent to produce a $(k_1+1)$-th coated material having in a surface layer thereof a $(k_1+1)$-th polyelectrolyte layer; and ($c_1$) performing step ($b_1$) at $k_1=1$ to produce a second coated material having in a surface layer thereof a second polyelectrolyte layer, or performing step ($b_1$) repeatedly from $k_1=1$ to $k_1=m$, wherein m is an integer of 2 or more, to produce a (m+1)-th coated material having in a surface layer thereof a (m+1)-th polyelectrolyte layer.

5. The composite material according to claim 4, wherein the second or (m+1)-th coated material has a zeta potential of 20 mV or more in absolute value.

6. The composite material according to claim 1, wherein the water absorbent material is a second or (n+1)-th coated material produced by a method comprising the following step $(a_2)$ to $(c_2)$:

($a_2$) contacting, in a predetermined solvent selected from a non-polar organic solvent, a polar organic solvent, and a mixed solvent of a polar organic solvent and water, a water absorbent particulate base material or water absorbent fibrous base material having a surface which is positively or negatively electrostatically charged in the predetermined solvent with a polyelectrolyte which is electrostatically charged to an electric charge opposite to that of the surface of the water absorbent particulate base material or water absorbent fibrous base material in the predetermined solvent to produce a first coated material having in a surface layer thereof a first polyelectrolyte layer;

($b_2$) contacting, in a predetermined solvent selected from a non-polar organic solvent, a polar organic solvent, and a mixed solvent of a polar organic solvent and water, a $k_2$-th coated material, wherein $k_2$ is an integer of 1 or more, having in a surface layer thereof a $k_2$-th polyelectrolyte layer which is positively or negatively electrostatically charged in the predetermined solvent with a polyelectrolyte which is electrostatically charged to an electric charge opposite to that of the $k_1$-th polyelectrolyte layer in the predetermined solvent to produce a $(k_2+1)$-th coated material having in a surface layer thereof a $(k_2+1)$-th polyelectrolyte layer; and ($c_2$) performing step ($b_2$) at $k_2=1$ to produce a second coated material having in a surface layer thereof a second polyelectrolyte layer, or performing step ($b_2$) repeatedly from $k_2=1$ to $k_2=n$, wherein n is an integer of 2 or more, to produce a (n+1)-th coated material having in a surface layer thereof a (n+1)-th polyelectrolyte layer.

7. The composite material according to claim 6, wherein the second or (n+1)-th coated material has a zeta potential of 20 mV or more in absolute value.

8. The composite material according to claim 1, wherein the polar organic solvent is a monohydric alcohol having 1 to 3 carbon atoms.

9. The composite material according to claim 1, wherein the fibrous base material of the substrate material is a thermoplastic resin fiber or aggregates thereof.

10. The composite material according to claim 1, wherein the fibrous base material or resinous base material of the substrate material is a nonwoven fabric sheet or resin sheet.

11. A method for producing a composite material for an absorbent article, comprising an adsorption step in which, in a predetermined solvent selected from a non-polar organic solvent, a polar organic solvent, and a mixed solvent of a polar organic solvent and water, a substrate material having a surface which is positively or negatively electrostatically charged in the predetermined solvent is contacted with a water absorbent material having a surface which is electrostatically charged to an electric charge opposite to that of the surface of the substrate material to adsorb the water absorbent material onto the substrate material by electrostatic interaction,
wherein the substrate material comprises a fibrous base material or resinous base material and a polyelectrolyte layer provided in a surface layer thereof, and/or, the water absorbent material has a water absorbent particulate base material or water absorbent fibrous base material and a polyelectrolyte layer provided in a surface layer thereof.

12. The production method according to claim 11, wherein the substrate material and/or the water absorbent material have a plurality of polyelectrolyte layers stacked together, and in the plurality of polyelectrolyte layers, polyelectrolyte layers that are electrostatically charged to electric charges opposite to each other in the predetermined solvent are adjacent to each other.

13. The production method according to claim 11, wherein the substrate material and water absorbent material have a zeta potential of 20 mV or more in absolute value in the predetermined solvent, and are balanced in charge.

14. The production method according to claim 11, wherein the substrate material is a second or (m+1)-th coated material produced by a method comprising the following steps ($a_1$) to ($c_1$):
($a_1$) contacting, in a predetermined solvent selected from water, a non-polar organic solvent, a polar organic solvent, and a mixed solvent of a polar organic solvent and water, a fibrous base material or resinous base material having a surface which is positively or negatively electrostatically charged in the predetermined solvent with a polyelectrolyte which is electrostatically charged to an electric charge opposite to that of the surface of the fibrous base material or resinous base material in the predetermined solvent to produce a first coated material having in a surface layer thereof a first polyelectrolyte layer;
($b_1$) contacting, in a predetermined solvent selected from water, a non-polar organic solvent, a polar organic solvent, and a mixed solvent of a polar organic solvent and water, a $k_1$-th coated material, wherein $k_1$ is an integer of 1 or more, having in a surface layer thereof a $k_1$-th polyelectrolyte layer which is positively or negatively electrostatically charged in the predetermined solvent with a polyelectrolyte which is electrostatically charged to an electric charge opposite to that of the $k_1$-th polyelectrolyte layer in the predetermined solvent to produce a ($k_1$+1)-th coated material having in a surface layer thereof a ($k_1$+1)-th polyelectrolyte layer; and
($c_1$) performing step ($b_1$) at $k_1$ =1 to produce a second coated material having in a surface layer thereof a second polyelectrolyte layer, or performing step ($b_1$) repeatedly from $k_1$ =1 to $k_1$ =m, wherein m is an integer of 2 or more, to produce a (m+1)-th coated material having in a surface layer thereof a (m+1)-th polyelectrolyte layer; and
wherein the second or (m+1)-th coated material is used as the substrate material.

15. The production method according to claim 14, wherein the second or (m+1)-th coated material has a zeta potential of 20 mV or more in absolute value.

16. The production method according to claim 11, comprising the following step ($a_2$) to ($c_2$):
($a_2$) contacting, in a predetermined solvent selected from a non-polar organic solvent, a polar organic solvent, and a mixed solvent of a polar organic solvent and water, a water absorbent particulate base material or water absorbent fibrous base material having a surface which is positively or negatively electrostatically charged in the predetermined solvent with a polyelectrolyte which is electrostatically charged to an electric charge opposite to that of the surface of the water absorbent particulate base material or water absorbent fibrous base material in the predetermined solvent to produce a first coated material having in a surface layer thereof a first polyelectrolyte layer;
($b_2$) contacting, in a predetermined solvent selected from a non-polar organic solvent, a polar organic solvent, and a mixed solvent of a polar organic solvent and water, a $k_2$-th coated material, wherein $k_2$ is an integer of 1 or more, having in a surface layer thereof a $k_2$-th polyelectrolyte layer which is positively or negatively electrostatically charged in the predetermined solvent with a polyelectrolyte which is electrostatically charged to an electric charge opposite to that of the $k_2$-th polyelectrolyte layer in the predetermined solvent to produce a ($k_2$+1)-th coated material having in a surface layer thereof a ($k_2$+1)-th polyelectrolyte layer; and
($c_2$) performing step ($b_2$) at $k_2$ =1 to produce a second coated material having in a surface layer thereof a second polyelectrolyte layer, or performing step ($b_2$) repeatedly from $k_2$ =1 to $k_2$ =n, wherein n is an integer of 2 or more, to produce a (n+1)-th coated material having in a surface layer thereof a (n+1)-th polyelectrolyte layer, wherein the second or (n+1)-th coated material is used as the water absorbent material.

17. The production method according to claim 16, wherein the second or (n+1)-th coated material has a zeta potential of 20 mV or more in absolute value.

18. The production method according to claim 11, wherein the polar organic solvent is a monohydric alcohol having 1 to 3 carbon atoms.

19. The production method according to claim 11, wherein the fibrous base material of the substrate material is a thermoplastic resin fiber or aggregates thereof.

20. The production method according to claim 11, wherein the fibrous base material or resinous base material of the substrate material is a nonwoven fabric sheet or resin sheet.

* * * * *